United States Patent
Hong et al.

(10) Patent No.: US 6,579,518 B2
(45) Date of Patent: Jun. 17, 2003

(54) CERAMIC DEODORIZER

(75) Inventors: Kug Sun Hong, 11-1502, Sampoong Apt., Secho 4-dong, Seocho-ku, Seoul 137-074, Seoul (KR); Dong-Wan Kim, Seoul (KR); Sang-Gu Kang, Jeonju (KR); Hyun-Seung Ryu, Seoul (KR); Su-Jin Kim, Seoul (KR); Dong-Ho Lee, Seoul (KR)

(73) Assignee: Kug Sun Hong, Seoul (KR)

( * ) Notice: Subject to any disclaimer, the term of this patent is extended or adjusted under 35 U.S.C. 154(b) by 0 days.

(21) Appl. No.: 09/765,576

(22) Filed: Jan. 22, 2001

(65) Prior Publication Data

US 2002/0031489 A1 Mar. 14, 2002

(30) Foreign Application Priority Data

Jul. 18, 2000 (KR) .......................... 2000-40968

(51) Int. Cl.[7] .......................... A61L 11/00; A61L 9/01; A61L 7/36; C11D 9/42; A61F 13/15
(52) U.S. Cl. .................. 424/76.5; 424/76.1; 424/67; 510/315; 604/367; 442/63
(58) Field of Search .................. 424/76.1, 67; 442/63; 510/315; 604/367

(56) References Cited

U.S. PATENT DOCUMENTS 4,097,935 A * 7/1978 Jarcho .......................... 3/1.9
5,567,231 A * 10/1996 Yokoo et al. .................. 96/153
6,051,215 A * 4/2000 van Nijnatten et al. .... 424/76.1

OTHER PUBLICATIONS

"Sulfur Compounds", Encyclopedia of Chemical Technology, vol. 23, p. 282–283.*
"Thiols", Encyclopedia of Chemical Technology, vol. 24, pp. 30–31.*
"Fertilizers", Encyclopedia of Chemical Technology, vol. 10, pp. 498.*

* cited by examiner

Primary Examiner—Jose' G. Dees
Assistant Examiner—Robert M DeWitty
(74) Attorney, Agent, or Firm—Shanks & Herbert

(57) ABSTRACT

Disclosed is a deodorizer composition comprising magnesium and calcium phosphate compounds, capable of effectively removing various malodorous components from the atmosphere.

3 Claims, 3 Drawing Sheets

CERAMIC DEODORIZER

This application claims priority to Republic of Korea Patent Application No.: 2000-40968 filed Jul. 18, 2000.

TECHNICAL FIELD

The present invention relates generally to a ceramic deodorizer, in particular, to a ceramic deodorizer comprising magnesium and calcium phosphate compounds being environmentally safe, capable of effectively removing various malodorous components.

RELATED ART

Generally, conventional methods for removing malodorous components comprise a sensory deodorization method using a masking agent and a neutralizing agent, a physical deodorization method using a wet washing and an adsorption, a biological deodorization method by use of microorganisms and a chemical deodorization method using precious metals.

Among said methods, the sensory method mainly using the masking agent cannot fundamentally remove malodorous components. The wet washing of the physical method is caused to produce wastewater and to increase maintenance costs. Also, the simple adsorption using an active carbon and charcoal is initially effective but adsorption ability is reduced as time goes by and the adsorbed malodorous components are easily desorbed by a change of surrounding environments. The biological method has disadvantages of requiring expensive facilities and maintenance of temperature and humidity ranges. The chemical method has used catalysts of expensive precious metals such as gold (Au), platinum (Pt), palladium (Pd), rhodium (Rd) and so on. However, the chemical method has recently begun using inexpensive metal oxides. For example, Korean Laid-open Pat. Appln. No. 98-013721 discloses a method for preparing a deodorization filter for refrigerator using metallic salt oxidants as adsorbents. Also, Korean Laid-open Pat. Appln. No. 99-016787 refers to a deodorization filter for refrigerator using catalysts such as copper, manganese and gold and an active carbon as adsorbent, while Korean Laid-open Pat. Appln. No. 99-0071045 refers to a deodorization filter for refrigerator using as adsorbent, honeycomb-shaped activated charcoal in which manganese dioxide and copper oxide and artificial enzyme catalysts are impregnated at certain proportions. But the metal oxides irritate skin and may be harmful to the human body. Accordingly, the oxides cannot be used as the deodorizer for home use owing to a safety problem.

To alleviate the problems, in recent years, calcium phosphate compounds, being harmless to the human body, have been used as deodorizers. Among the calcium phosphate compounds, non-stoichiometric structure of appetite ($Ca_{10-x}H_x(PO_4)_6(OH)_{2-x}$) or tricalcium phosphate (TCP, $Ca_3(PO_4)_2$) is mainly used. Japanese Laid-Open Pat. Appln. No. 5309266 discloses an apatite hydroxide having excellent deodorization effect versus malodorous lower fatty acid occurring in food wastes. Additionally, in order to improve an deodorization ability versus other malodorous components in addition to lower fatty acids, Japanese Laid-Open Pat. Appln. No. 10118167 discloses that calcium phosphate compound is added with iron, copper, zinc, nickel and aluminum for use as a deodorizer, while Japanese Laid-open Pat. Appln. No. 8126690 discloses that silver is ion-exchanged or adsorbed in the calcium phosphate compound for use as a deodorizer. In addition, Japanese Laid-Open Pat. Appln. No. 2237639 discloses that $Zn^{2+}$, $Cu^{2+}$, $Fe^{2+}$, $Co^{2+}$, $Ni^{2+}$, $Sn^{2+}$, $Pb^{2+}$ and $Cd^{2+}$ are ion-exchanged in the calcium phosphate compounds for use as a deodorizer. U.S. Pat. No. 4,988,505 discloses a deodorizer which comprises a colloidal antimony pentoxide that is effective to deodorize a basic gas, an acidic gas, and an organic solvent gas. But the metal oxides, metal ions and colloidal antimony pentoxide have toxic properties so that a danger exists to the human body and environment, and their deodorization ability versus various malodorous components is limited.

SUMMARY OF THE INVENTION

Accordingly, an object of the present invention for alleviating the problems as described above is to provide a deodorizer composition, that is environmentally safe, harmless to the human body, and capable of removing malodors from various sources.

For the invention, the calcium phosphate compound may be selected from the group consisting of apatite, monocalcium phosphate ($CaHPO_4$), tricalcium phosphate (TCP), octacalcium phosphate (OCP), and mixtures thereof.

In another aspect of the present invention, a deodorizer composition comprising a mixture of at least one magnesium compound and at least one calcium phosphate compound is provided.

In still another aspect of the present invention, a ceramic deodorizer prepared by heating the compositions is provided.

According to another aspect of the present invention, is provided a process for preparing the deodorizer composition, which comprises the steps of:

providing a solution of magnesium nitrate in phosphoric acid solution;

adding calcium hydroxide to the solution to give a mixture; and allowing the mixture to stand for several hours.

The composition can be heat treated to give the ceramic deordorizer.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

Figure 1:
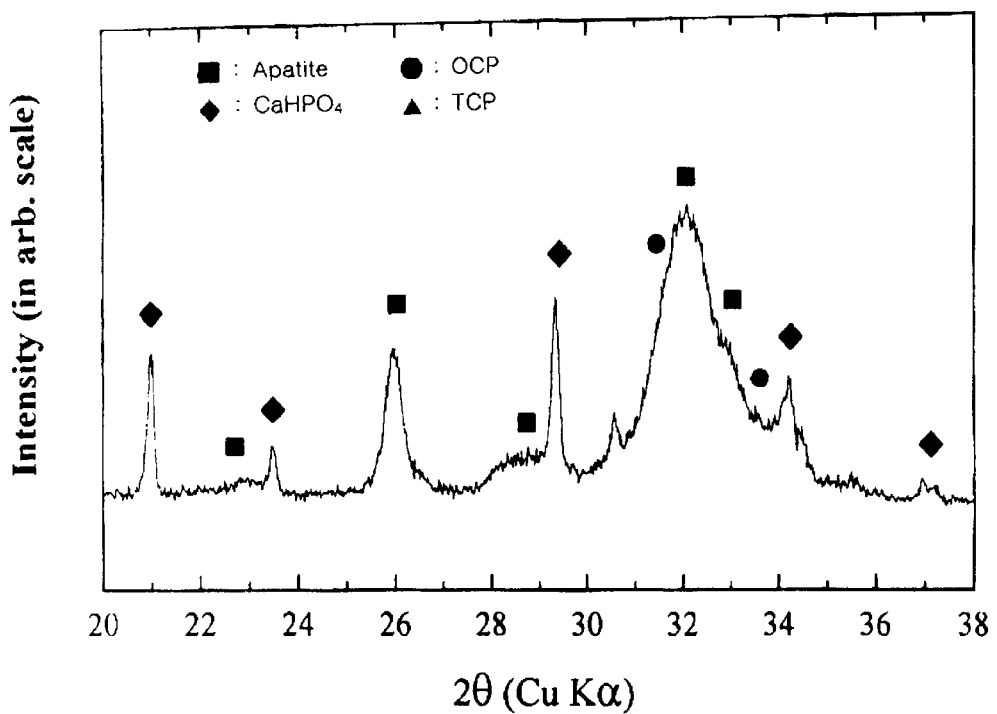
FIG. 1 shows a composition of the deodorizer powder of Example 1 as measured by X-ray diffraction.

The present invention provides a deodorizer composition having at least one calcium phosphate compound selected from the group consisting of apatite, monocalcium phosphate ($CaHPO_4$), tricalcium phosphate (TCP), octacalcium phosphate (OCP) or mixtures thereof, a part of calcium in the calcium phosphate compound being replaced with magnesium.

In addition, the present invention provides a deodorizer composition prepared by adding magnesium to calcium phosphate compounds selected from the group consisting of apatite, monocalcium phosphate ($CaHPO_4$), tricalcium phosphate (TCP), octacalcium phosphate (OCP) or mixtures thereof.

The present invention further provides ceramic deodorizers prepared from these compositions.

Non-stoichiometric structure of apatites useful as a deodorizer has hydrogen ions included in a lattice structure such that a lower fatty acid, a main source of malodors in house, is adsorbed onto the hydrogen ion. But, though hydrogen ions are included in apatite, which is a basic compound, the quantity of the included hydrogen ions is not enough due to non-stoichiometry to adsorbfully the lower fatty acid. Accordingly, monocalcium phosphate and octacalcium phosphate (OCP, $Ca_8(HPO_4)_2(PO_4)_4 \cdot 5H_2O$) in which large quantities of hydrogen ions are included in the lattice of the compound structure, may be mixed at suitable proportions so that great quantities of lower fatty acids can be adsorbed. In particular, monocalcium phosphate is an acidic compound so that the basic malodorous components, such as ammonia, can be effectively neutralized. Also, apatite including a functional group selected from the group consisting of hydroxide group, carbonate group, chloride ion, fluoride ion or mixtures thereof can neutralize the acidic malodorous components. Consequently, calcium phosphate composition comprising monocalcium phosphate, OCP, TCP and apatite may preferably be used as raw materials of hybrid-type deodorizers, capable of removing both acidic and basic malodorous components.

Effects of substitution or addition of magnesium in calcium phosphate compounds of the present invention are as follows.

For removing hydrogen sulphide ($H_2S$), unable to be removed by use of a conventional apatite or calcium phosphate compound, magnesium having excellent adsorption properties for hydrogen sulphide is substituted for calcium in calcium phosphate compounds, or magnesium compounds such as magnesia or magnesium hydroxide are added to calcium phosphate compound.

Magnesium as a structural ingredient of the human body is contained in bones, body fluids and muscles and is harmless to the human body, compared to metal elements such as Cu, Ni, Zn and the like, used as metallic salt catalysts for common deodorizers. In addition, magnesium is a divalent cation, like calcium so that calcium in not only apatite but also other calcium phosphate compounds may be easily replaced with magnesium.

In addition, magnesium affects a process for synthesizing apatite powders. Apatite useful as a raw material of deodorizers is synthesized by a neutralization of calcium hydroxide and phosphoric acid in aqueous solution, in which monocalcium phosphate is hydrolyzed or TCP is produced to be converted into apatite. At this point, a conversion of TCP into apatite is faster than that of monocalcium phosphate into apatite. When magnesium salts are added to an aqueous solution of synthetic apatite, TCP can be readily produced to increase an amount of apatite and to reduce a time period for synthesis. When being substituted for calcium, magnesium, which is smaller in atomic size than calcium, disturbs a stoichiometrically stable structure of apatite while a non-stoichiometric structure of apatite is stabilized. When magnesium is replaced at high amounts, TCP is extremely stabilized so that pure TCP without apatite can be synthesized according to need.

In the calcium phosphate composition consisting of monocalcium phosphate, OCP, TCP and apatite according to the present invention, when the apatite amounts to 30–80 wt % of the calcium phosphate composition, and magnesium is preferably substituted for calcium at an atomic ratio of 0.01–20. If the ratio is less than 0.01, the substituted compound has very similar deodorization performance to the unsubstituted compound because the substituted amount is very much small. On the other hand, if the ratio exceeds 20, the substituted amount of magnesium is increased so that more TCP is produced than apatite, but this TCP has the disadvantage of not converting into apatite because excess magnesium stabilizes TCP.

Meanwhile, when TCP amounts to 30–80 wt % of the calcium phosphate composition, It has been founded that magnesium is substituted for calcium in an atomic ratio of 10–90 and preferably in an atomic ratio of 15–60. If the ratio is less than 10, apatite may be the major component in the calcium phosphate composition. On the other hand, if the ratio exceeds 90, a considerable amount of magnesium may not take part in a substitution reaction, remaining unreacted.

Instead of replacing calcium in calcium phosphate compositions with magnesium, magnesium compounds such as magnesia, magnesium hydroxide and the like may be mixed with the calcium phosphate compound. As such, it is desired to add and to mix at a weight ratio of 5–85 and preferably at a weight ratio of 10–65.

If the weight ratio is less than 5, the magnesium compound-added calcium phosphate compound has a very similar deodorization performance to that of magnesium compound-not added compound. On the other hand, if the weight ratio exceeds 85, the calcium phosphate compound cannot greatly deodorize malodorous components because excess magnesium compound is present in the calcium phosphate compound.

Substitution or addition of magnesium in calcium phosphate compounds can not only remove hydrogen sulphide not removed by a conventional calcium phosphate-based deodorizer, but also increase the adsorption and decomposition effects of various malodorous components of acidic and basic substances, as well as being easily synthesized.

The deodorizer composition may be subjected to heat treatment to give ceramic deodorizer. The heat treatment may be performed at 600° C. for 1h.

A better understanding of the present invention may be obtained in light of the following examples which are set forth to illustrate, but are not to be construed to limit the present invention.

EXAMPLE 1

12.95 g of magnesium nitrate ($Mg(NO_3)_2 \cdot 8H_2O$) was dissolved in 500 mL of phosphoric acid ($H_3PO_4$). Thereto was added 1M calcium hydroxide ($Ca(OH)_2$) such that molar ratio of the whole cations to phosphate anions ($PO_4^{3-}$) was 1.67, and the total concentration was 0.5 M. As calcium hydroxide solution was added, the pH of the solution was drastically increased from 0.2 up to 13, after which it was maintained at a pH range of 12 to 13. The reaction mixture was incubated at 30° C. for 4 hours, filtered and then repeatedly washed with distilled water, followed by drying at normal temperature.

It was found that the dried powder was a mixture of 40 wt % of apatite, 30 wt % of monocalcium phosphate, 10 wt % of OCP and 20 wt % of TCP by X-ray diffraction (XRD) analysis. As a result of analysis of cation components by use of EDAX in electronic microscope, it could be seen that an atomic ratio of magnesium to calcium in accordance with detection of magnesium was 96 to 4 so that magnesium was substituted for calcium. The powder was subjected to heat treatment at 900° C. for 20 hours to obtain a stoichiometric structure of compound. The XRD quantitative analysis was conducted for the compound, whereby the molar ratio of the whole cations versus phosphate ion was found to be 1.53. The result is shown in FIG. 1.

COMPARATIVE EXAMPLE 1

The same procedure as in Example 1 was repeated except that magnesium nitrate was not added.

With a heavy malodor represented by 10, and no malodor by 0, the malodor degrees were represented by numbers of 0–10. The mean value was determined to signify the deodorization performance. The results are given in Table 1, below.

TABLE 1

|  | Ex. 1 | | | Ex. 2 | | | Ex. 3 | | | C. Ex. 1 | | |
| --- | --- | --- | --- | --- | --- | --- | --- | --- | --- | --- | --- | --- |
|  | 0.5 h | 3 h | 5 h | 0.5 h | 3 h | 5 h | 0.5 h | 3 h | 5 h | 0.5 h | 3 h | 5 h |
| Kimchi (acidic) | 4.0 | 2.0 | 0 | 4.3 | 1.9 | 0 | 4.5 | 2.2 | 0 | 8.0 | 4.0 | 2.0 |
| Cigarette (acidic) | 5.5 | 2.2 | 1.0 | 5.2 | 2.5 | 1.2 | 5.4 | 2.4 | 1.0 | 7.0 | 4.0 | 2.5 |
| Ammonia (basic) | 5.0 | 1.7 | 0.5 | 5.3 | 1.9 | 0.4 | 5.2 | 2.0 | 0.5 | 8.5 | 8.2 | 7.9 |
| Hydrogen Sulphide | 7.0 | 3.5 | 2.6 | 7.2 | 3.7 | 2.4 | 6.5 | 4.2 | 2.6 | 10.0 | 9.0 | 9.0 |

Figure 2:
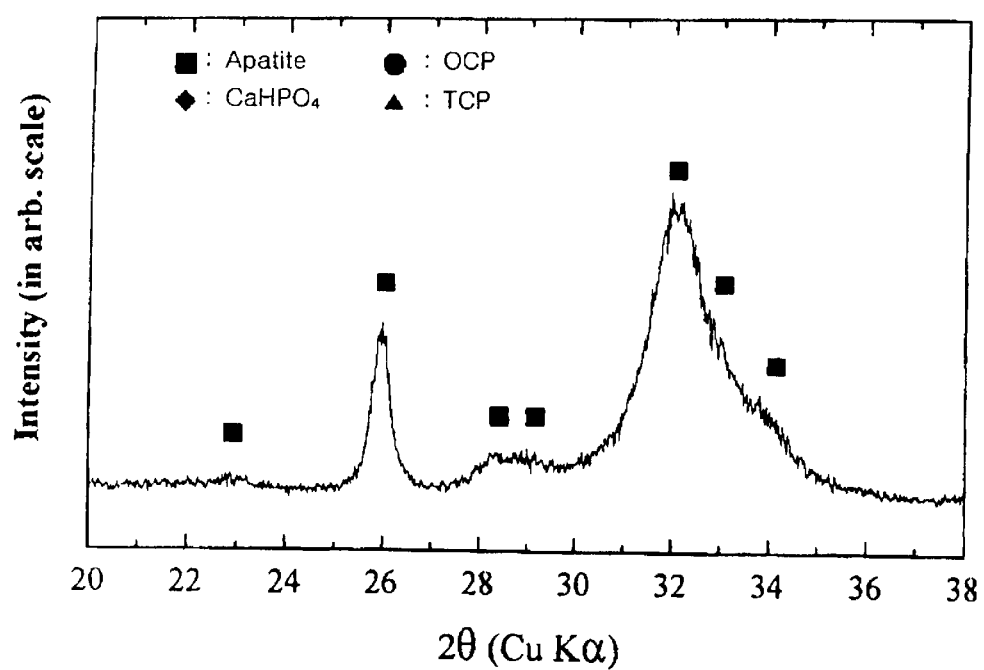
FIG. 2 shows a composition of the deodorizer powder of Comparative Example 1 as measured by X-ray diffraction.
Figure 3:
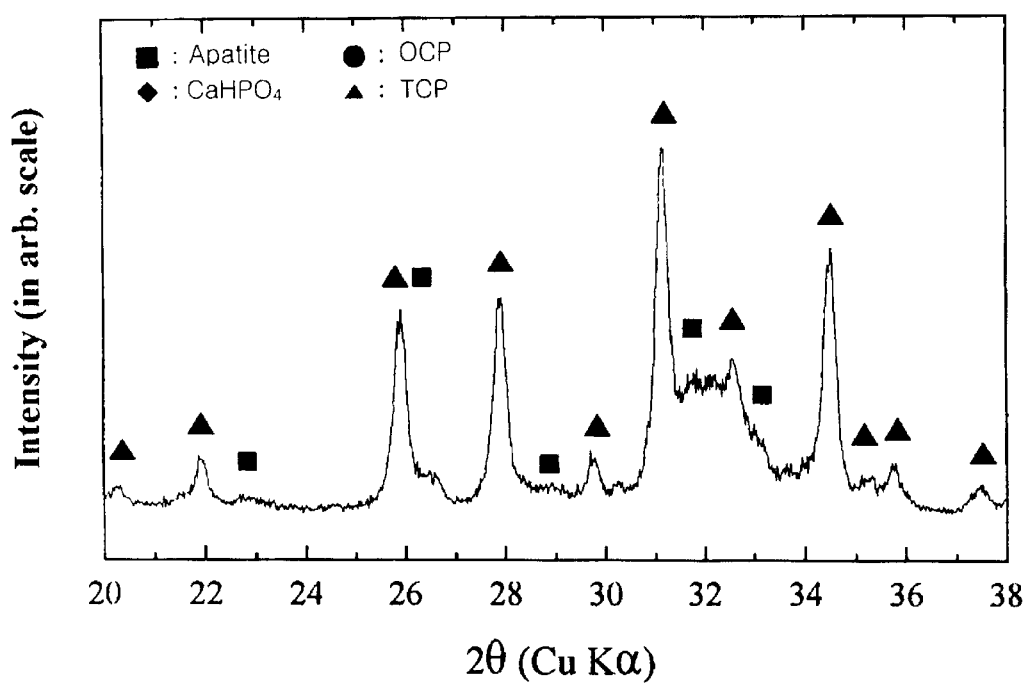
FIG. 3 shows a composition of the deodorizer powder of Example 2 as measured by X-ray diffraction.

The dried powder was observed with the XRD, whereby the presence of only pure apatite was observed. In the cation component analysis using EDAX, magnesium was not detected. The powder was thermally treated to yield the stoichiometric structure of compound. It was found that the molar ratio of calcium ion versus phosphate ion was 1.63 according to the XRD quantitative analysis of the compound. The result is given in FIG. 2.

EXAMPLE 2

The same procedure as in Example 1 was repeated except that 25.90 g of magnesium nitrate ($Mg(NO_4)_2 \cdot 8H_2O$) was used.

The dried powder was quantitatively analyzed with the XRD. As a result, it was found that the powder was composed of a mixture of 70 wt % of TCP and 30 wt % of apatite. According to the cation component analysis by use of the EDAX, it could be seen that magnesium was detected and the atomic ratio of magnesium to calcium was 88 to 12, whereby magnesium was substituted for calcium. The powder was thermally treated to obtain the stoichiometric structure of compound. The ratio of the whole cations versus phosphate ion was 1.55 in accordance with the XRD quantitative analysis of the compound. The mixture of TCP and apatite was added with additional synthetic monocalcium phosphate such that the final composition was 45% TCP, 18% apatite and 37% monocalcium phosphate.

EXAMPLE 3

20 g of calcium phosphate mixture of the comparative example 1 was added with 20 g of magnesium oxide (MgO, Junsei, Japan), being a commercial reagent, followed by conducting a ball milling for 24 hours to totally mix and dry the components.

Deodorization Performance Test

The deodorizer powders prepared in the examples 1, 2 and 3, and the comparative example 1 were finely ground by use of a mortar and then charged to chalets. The chalets was put into 36 collection bottles in which noxious items, such as Kimchi, a cigarette-butt and ammonia, had been left for one day and then taken out. 10 persons chosen for assay smelled the collection bottles at a predetermined period of time, and individually determined degrees of malodor in the bottles.

From the results of table 1, it can be seen that malodorous components, such as Kimchi, cigarette, ammonia and hydrogen sulphide odors, are much faster removed in the examples 1 to 3, compared to the comparative example 1. Not only acidic malodorous components such as Kimchi, cigarette and the like, but also basic malodorous components including ammonia, being difficult to treat only by use of apatite, have been effectively removed. Also, examples 1 and 2, where calcium in calcium phosphate composition is replaced with magnesium, have a similar deodorization capability to that of example 3 where magnesium oxide is added. In addition, it can be seen that example 1, where apatite is a major component, has a similar deodorization performance to that of example 2 where TCP is a major component.

As described above, the deodorizer is prepared by substituting magnesium for calcium in calcium phosphate compounds or adding magnesium to calcium phosphate compounds, being a mixture of basic substances mainly comprising apatite or TCP and acidic substances including monocalcium phosphate. The deodorizer of the present invention being non-toxic is harmless to the human body, and also can be safely used as deodorizers for industry and for home, because of removing malodorous acidic and basic components and hydrogen sulphide not removed by use of a conventional deodorizer only including apatite and TCP.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A deodorizer composition and deodorizing elements thereof,
  comprising at least one calcium phosphate compound selected from the group consisting of apatite, monocalcium phosphate ($CaHPO_4$), tricalcium phosphate (TCP), and octacalcium phosphate (OCP);
  wherein calcium ions in said calcium phosphate is replaced by magnesium ions in an atomic ratio of from 0.01 to about 20', and said apatite has a functional group selected from the group consisting of hydroxyl group, carbonate group, chloride ion, fluoride ion and mixtures thereof; and said apatite amounting to 30–80 wt %, based on the total amount of the deodorizer composition.

2. A deodorizer composition and deodorizing elements thereof, comprising at least one calcium phosphate compound selected from the group consisting of apatite, monocalcium phosphate ($CaHPO_4$), tricalcium phosphate (TCP), and octacalcium phosphate (OCP);

wherein calcium ions in said calcium phosphate is replaced by magnesium ions in an atomic ratio of from 10 to about 90, and said apatite has a functional group selected from the group consisting of hydroxyl group, carbonate group, chloride ion, fluoride ion and mixtures thereof; and said TCP amounting to 30–80 wt %, based on the total amount of the deodorizer composition.

3. A deodorizer composition as in any one of the preceding claims, wherein the composition is in the form of a ceramic deodorizer.

* * * * *